ID: 3,968,158 July 6, 1976

United States Patent
Parker

[54] PROCESS FOR PREPARING PERFLUOROGUANIDINE AND DIFLUOROUREA

[75] Inventor: Charles O. Parker, Huntsville, Ala.

[73] Assignee: Rohm and Haas Company, Philadelphia, Pa.

[22] Filed: Apr. 12, 1963

[21] Appl. No.: 273,263

[52] U.S. Cl. .................. 260/553 R; 260/564 R; 149/109.4
[51] Int. Cl.[2] ............. C07C 127/00; C07C 129/08
[58] Field of Search ................ 260/563 R, 564 R

[56] References Cited
UNITED STATES PATENTS 3,228,936  1/1966  Davis et al. .................. 260/553 X

*Primary Examiner*—Leland A. Sebastian

EXEMPLARY CLAIM

1. A process for the preparation of difluorourea and perfluoroguanidine which comprises reacting in aqueous solution fluorine with a material selected from the group consisting of guanidine and water-soluble salts of guanidine.

5 Claims, No Drawings

PROCESS FOR PREPARING PERFLUOROGUANIDINE AND DIFLUOROUREA

This invention concerns a process for the preparation of perfluoroguanidine and difluorourea. More particularly, it concerns the direct fluorination of an aqueous solution of guanidine or guanidine salts to produce gaseous perfluoroguanidine and difluorourea which remains in the aqueous phase.

Difluorourea has been prepared previously by the direct fluorination of urea in aqueous solution but no perfluoroguanidine is produced.

Perfluoroguanidine has been previously prepared by the direct fluorination of guanidine salts in the dry state. In this process, however, the formation of perfluoroguanidine is unavoidably accompanied by the formation of other volatile fluorinated compounds, principally tris(difluoroamino)fluoromethane. Since perfluoroguanidine and tris(difluoroamino)fluoromethane are formed in relatively similar proportions, and since separation of these compounds is tedious and expensive, and most of the known methods result in partial destruction of the perfluoroguanidine, preparation of pure perfluoroguanidine by the prior art method is difficult and expensive.

Difluorourea is one of the most desirable precursors for the preparation of difluoramine. Difluoramine is well-known as a versatile intermediate for the preparation of a great many difluoramino compounds which have recognized utility as oxidizers, binders, plasticizers and monopropellants for rocket propellant compositions.

Typical of such compounds are:

2,2-bis(difluoroamino)propane, $CH_3—C(NF_2)_2—CH_3$,
1-nitrato-2,2-bis(difluoroamino)propane, $CH_3—C(NF_2)_2—CH_2ONO_2$,
2,2-bis(difluoroamino)propyl acrylate, $CH_2=CH—COOCH_2—C(NF_2)_2CH_3$, and
2,2-bis(difluoroamino)propane-1,3-diol dinitrate, $O_2NO—CH_2C(NF_2)_2—CH_2ONO_2$.

There are only a few of the high energy compounds which can be prepared using difluoramine, $HNF_2$.

Perfluoroguanidine is also useful as an intermediate for the preparation of compounds which possess great potential and which are valuable as constituents in rocket propellant compositions. A few compounds typical of these high energy compositions are:

tetrakis(difluoroamino)methane, $C(NF_2)_4$,
tris(difluoroamino)methyl isocyanate, $(F_2N)_3C—N=C=O$,
N-fluoro-N-hydro-bis(difluoroamino)methyl isocyanate, $(F_2N)_2C(NFH)NCO$, and
N-fluoro-N-hydro-bis(difluoroamino)methyl methyl ether, $(F_2N)_2C(NFH)OCH_3$.

The process of the present invention is simple and easy to perform and control using a simple apparatus. The raw materials employed, namely fluorine, a diluent gas, guanidine salts in water, are all inexpensive. The water is used not only as a reaction medium, but also as a heat transfer agent.

In contrast to the prior art processes, the process of the present invention produces perfluoroguanidine, accompanied by the concurrent formation of gaseous products which may be separated easily from the perfluoroguanidine permitting isolation of the pure product or of product sufficiently pure for technical or synthetic use. Gases (boiling points in parenthesis) which accompany the formation of perfluoroguanidine ($-2°$ to $+2°$) are carbon dioxide ($-78°$), nitric oxide ($-151°$), nitrogen dioxide, nitrogen tetroxide ($21°$), fluorine nitrate ($-42°$), nitrogen trifluoride ($-129°$), nitrous oxide ($-88.5°$), silicon tetrafluoride ($-95°$) and carbon tetrafluoride ($-128°$). It will be seen from inspection of the boiling points of the components of the gaseous mixture that temperatures of from $-110°$ to $-130°$ will reduce the vapor pressures of the perfluoroguanidine and the nitrogen tetroxide to very low values while all the other species present will have sufficiently high vapor pressures to permit their removal at low pressure. It will be apparent that then by use of temperatures of about $-80°$ a separation of the nitrogen tetroxide from perfluoroguanidine may be made in like manner. Purification procedures of this sort were in fact found to give samples of perfluoroguanidine contaminated with not over 0.5% of nitrogen dioxide, this value being the maximum amount of $NO_2$ which escapes detection in a mass spectrometer but which is detectable by infrared or ultraviolet spectrophotometry.

The inert gas diluent can be nitrogen, argon or helium, but the use of helium is preferred in order to avoid condensing anything but product gases when using liquid nitrogen cooled traps. Subsequent experimental work has shown that nitrogen is in no way objectionable for use as the diluent gas. The use of an inert diluent gas serves two functions, namely controlling the exotherm, as well as facilitating removal of the gaseous products from the reaction mixture.

Various salts of guanidine may be used as substrates for fluorination but no advantage was derived by using anything other than guanidinium hydrofluoride, which was made simply by adding aqueous hydrofluoric acid to an aqueous solution of guanidine carbonate until the solution was neutral. Many anions present in solution undergo fluorination and can give rise to fluorinated species which can cause undesirable consumption of fluorine and which may require special treatment to separate them from the desired products of reaction, namely difluorourea and perfluoroguanidine. For this reason, chloride, bromide, iodide, sulfate, nitrate and any carboxylate salts are not preferred. Both guanidine carbonate and bicarbonate were used and although perfluoroguanidine was produced, there were two serious objections to the use of such salts. As the reaction with fluorine progressed, the carbon dioxide equivalent to the carbonate or bicarbonate used was displaced from the solution and was condensed when liquid nitrogen cooled traps were used, and it frequently plugged the traps and caused undesirable pressure build up. The other objection is that solutions of guanidine carbonate particularly have a relatively high pH and this caused decomposition of difluorourea formed until the pH of the reaction mixture became reduced by the hydrogen fluoride formed as a by-product of the direct fluorination.

As indicated hereinbefore, one of the desired products, namely difluorourea, can be at least partially destroyed if the pH of the solution is not controlled. The pH ranges from 2 to 11, and a preferred range is from 4 to 8.

The same apparatus and procedure was used for all of the following examples. The guanidine salt dissolved in distilled water was placed in a Pyrex 3-necked creased flask (reactor) which was equipped with a Trubore stirrer, a gas inlet tube and a Y-tube which mounted a thermometer dipping into the solution and a gas outlet tube. The gas inlet tube consisted of ¼ inch copper tubing connected to a short length of 1 mm. bore capillary tubing by a Tygon sleeve. The glass capillary tubing served as an orifice as the gas-liquid interface. The gas outlet tube connected the reactor with a series of glass U-tubes which were attached to a vacuum manifold constructed so as to permit expansion, measurement, sampling and purification of product gases trapped in the U-tube by means of condensing cold baths. The reactor was cooled to 0° to 5° during introduction of fluorine by immersion in an ice-water bath.

Fluorine was taken from a cylinder, bled into a metered stream of helium, conducted through a length of pipe packed with sodium fluoride pellets, through a second rotameter, through a sequence of tees and valves and into the reactor. The tees and valves permitted mixing measured flow rates of helium and fluoride which were vented before and after an accurately measured time interval during which the gas mixture was diverted into the reactor. Thereby the quantity of fluorine used in any experiment could be accurately regulated.

After termination of the passage of fluorine into the reactor, the apparatus was flushed with helium until all product gases and fluorine were removed from the reactor and either condensed in the cold traps or swept through them. The aqueous solution in the reactor was measured volumetrically and was transferred into a polyethylene vessel and kept cold, preferably below 0° C., to retard decomposition of the reactive products therein.

The yield of difluorourea was measured by determination of the oxidation equivalent value of the aqueous solution. For example, 10 ml. of the aqueous reaction mixture was diluted to 100 ml. volumetrically using ice-cold distilled water and scrupulously cleaned glassware. For analysis, 1 ml. portions of this solution were pipetted into 25 ml. portions of distilled water in which was dissolved 0.5 gram of potassium iodide and 1 ml. of acetic acid. After waiting for 15 to 20 minutes to insure completeness of reaction, the resulting solution of iodine was titrated against standardized sodium thiosulfate solution. In separate determinations, 1.85 ml. and 1.86 ml. of 0.0426 N sodium thiosulfate solution were required. Thus, the reaction mixture solution contained $(1.86) \times (0.0426)(10) = 0.792$ milliequivalents/ml. of oxidizer. The final volume of reaction mixture solution was 328 ml. and so the quantity of oxidizer produced was $328 \times 0.792 = 259.8$ milliequivalents. The oxidation stoichiometry of the reaction of difluorourea with potassium iodide in aqueous acidic media is:

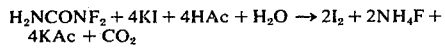

from which it will be seen that one mole of difluorourea oxidizes four iodide ions and that, therefore, the number of millimoles of difluorourea will be one-fourth of the oxidation titer value, or 64.9 in the example given.

Difluorourea was isolated as a pure chemical species from reaction mixtures by extraction of the cold, aqueous solution of fluorinated guanidinium hydrofluoride with ethyl acetate, repeating the extraction until the oxidation titer of the aqueous solution had dropped to a small fraction of its initial value, which usually required four to five extractions with one-fourth volumes of solvent. The combined portions of extraction solvent were dried with anhydrous sodium sulfate and the solvent evaporated at room temperature or below. The residue remaining after evaporation of the solvent was subjected to reduced pressures of less than 1 mm., usually of from 10 to 20 microns (0.010 – 0.020 mm.), whereupon difluorourea evaporated from the residue and was condensed in a trap cooled to −15°. By suitable techniques including repetition of the sublimation process and fractional condensation of the evaporating material (to effect separation from water and acetic acid), difluorourea was isolated as a white, crystalline solid, m.p. 42.5° – 43.5° (sealed tube) when handled in an atmosphere of 58% relative humidity (or less).

For all synthetic purposes, difluorourea is never isolated, but is converted to difluoramine by addition of mineral acid to the crude, aqueous solution of fluorinated guanidine hydrofluoride (or of fluorinated urea) followed by heating the solution to drive off the difluoramine, which is collected by condensation in a cold trap. The yields of pure difluoramine obtained in this manner correspond to within 10 to 15% of the theoretical amount expected based on the quantity of difluorourea indicated by the oxidation titer of the solution determined as described above, thereby further confirming the identity as difluorourea of the active species giving the oxidation titer.

That portion of the volatile gaseous mixture escaping from the reactor during fluorination of aqueous solutions of guanidine salts which was found condensed in traps cooled to temperatures of −196° contained perfluoroguanidine together with other gaseous fragments formed during the reaction. While trap temperatures as low as −78° sufficed to condense a portion of perfluoroguanidine (which has a vapor pressure of about 15 mm at −78°) formed during the reaction and trap temperatures appreciably below −78° could be used to trap it still more effectively, temperatures of at least −120° to −130° were required to prevent significant loss of perfluoroguanidine by entrainment with the sweep of diluent gas.

The product gases which were found condensed in a trap cooled to −196° were separated from the atmosphere in the trap and from condensed gases having appreciable vapor pressure at −196°, such as nitrogen, oxygen and the like by pumping on the trap until the pressure was reduced to less than 0.1 mm. The trap was then allowed to warm to −78° to −80° while collecting the expanding gases in a calibrated evacuated bulb. A sample of the expanded gases was found to consist of 70% $CO_2$, 10% $NF_3$, 6% $NO_2$, and 6.6% $O_2$ by mass spectrometric analysis. The mass spectrometer does not distinguish fluorine nitrate, $FONO_2$, a species found to be present by examination of the infrared spectrum of the gases, because it is characteristically decomposed by the hot filament in the mass spectrometer. Perfluoroguanidine, although present in small quantity in this mixture of gases, is not detectable with certainty as such because its identification by mass spectrometric analysis is based on observation of mass peaks of weak intensity in the spectrum of fragments obtained from a sample of relatively pure gas. The major intensity fragment mass peaks given by perfluoroguanidine cannot be distinguished from identical fragment mass peaks coming from $NF_3$, for example, which is present in much greater quantity.

The results of a series of reactions carried out as set forth hereinbefore appear in TABLE I:

TABLE I

| | Guanidinium Salt | Weight in Grams | Millimoles | Grams of Water | $F_2$ l./hr. | He l./hr. | $F_2$ m.moles | PFG m.moles | DFU m.moles |
|---|---|---|---|---|---|---|---|---|---|
| (1) | $CO_3^=$ | 10 | 55 | 300 | 3 | 6 | 300 | 12.5 | 64.9 |
| (2) | $CO_3^=$ | 10 | 55 | 250 | 3 | 6 | 330 | — | 80 |
| (3) | $F^-$ | 15.8 | 200 | 300 | 3 | 9 | 400 | 4.3 | 89 |
| (4) | $F^-$ | 15.8 | 200 | 300 | 3 | 9 | 400 | 3.5 | 93.1 |
| (5) | $F^-$ | 15.8 | 200 | 300 | 3 | 9 | 400 | | 71.9 |
| (6) | $F^-$ | 15.8 | 200 | 300 | 3 | 9 | 600 | 10.4 | 134 |
| (7) | $F^-$ | 15.8 | 200 | 300 | 3 | 9 | 600 | | 143 |
| (8) | $F^-$ | 15.8 | 200 | 290 | 3 | 9 | 400 | 2.2 | 109 |

NOTE:
Guanidinium carbonate, $(CH_6N_3)_2CO_3$, M.W. 180, contains two equivalents of guanidine per mole. Thus theoretical yields for Nos. 1, 2 are 110 m.moles. DFU. Guanidinium hydrofluoride is $CH_6N_3F$, M.W. 79, and theoretical yields for Nos. 3–8 are 200 m.mole DFU, based on guanidine.

The expanded gases were quickly condensed away from above the species present as condensed liquid at −78° and the condensed liquid was allowed to evaporate, all gases passing through an evacuated trap cooled to −130° C. When this process was finished, material condensed in the −130° trap was expanded separately from that material which had passed through and which was found condensed in another trap cooled to −196°. The latter fraction was expanded and measured by volume and a sample of it was subjected to mass spectrometric analysis which showed it to consist of carbon dioxide (98%) and nitrogen trifluoride (2%). The infrared spectrum of a sample of the −130° condensate was found to correspond exactly with the infrared absorption bands of perfluoroguanidine. Another sample subjected to mass spectrometric analysis exhibited a mass cracking pattern with intensity of m/e ratios matching the values reported for perfluoroguanidine.

I claim:

1. A process for the preparation of difluorourea and perfluoroguanidine which comprises reacting in aqueous solution fluorine with a material selected from the group consisting of guanidine and water-soluble salts of guanidine.

2. A process as set forth in claim 1 in which an inert diluent gas is admixed with the fluorine prior to passage into the aqueous solution.

3. A process as set forth in claim 2 in which the inert diluent gas is selected from the group consisting of helium, argon and nitrogen.

4. A process as set forth in claim 1 in which the guanidine compound is guanidine hydrofluoride.

5. A process as set forth in claim 1 in which the pH of the aqueous solution is in the range 4 to 8.

* * * * *